(12) United States Patent
Takata et al.

(10) Patent No.: US 8,242,302 B2
(45) Date of Patent: Aug. 14, 2012

(54) INHIBITOR OF ISCHEMIC DISORDERS

(75) Inventors: Jiro Takata, Fukuoka (JP); Kenichi Mishima, Fukuoka (JP); Manabu Nakashima, Fukuoka (JP); Katsunori Iwasaki, Fukuoka (JP); Kazuhisa Matsunaga, Fukuoka (JP); Yoshiharu Karube, Fukuoka (JP); Michihiro Fujiwara, Fukuoka (JP)

(73) Assignee: Fukuoka University, Fukuoka-shi, Fukuoka (JP)

( * ) Notice: Subject to any disclaimer, the term of this patent is extended or adjusted under 35 U.S.C. 154(b) by 231 days.

(21) Appl. No.: 12/675,129

(22) PCT Filed: Sep. 1, 2008

(86) PCT No.: PCT/JP2008/065680
§ 371 (c)(1),
(2), (4) Date: Feb. 25, 2010

(87) PCT Pub. No.: WO2009/028707
PCT Pub. Date: Mar. 5, 2009

(65) Prior Publication Data
US 2010/0217006 A1    Aug. 26, 2010

(30) Foreign Application Priority Data
Aug. 31, 2007   (JP) ................................. 2007-225021

(51) Int. Cl.
C07C 229/12    (2006.01)
C07D 213/79    (2006.01)
A61K 31/223    (2006.01)
(52) U.S. Cl. ......... 560/155; 514/354; 514/551; 546/326
(58) Field of Classification Search ................... 560/155; 546/326; 514/354, 551
See application file for complete search history.

(56) References Cited

U.S. PATENT DOCUMENTS
2003/0027857 A1    2/2003   Takata et al.
2003/0187059 A1    10/2003  Levin et al.

FOREIGN PATENT DOCUMENTS
JP    2000-268885    9/2000
JP    2002-80475     3/2002
JP    2003-292413    10/2003
JP    2005-119991    5/2005

OTHER PUBLICATIONS

Ferdinandy et al, Molecular and Cellular Biochemistry, vol. 186, p. 27-34 (1998).*
International Preliminary Report on Patentability for corresponding PCT/JP2008/065680 mailed May 20, 2010, seven pages.
International Search Report for corresponding PCT/JP2008/065680, mailed Nov. 18, 2008, six pages.
Japanese Abstract for Publication No. 2003-292413 published Oct. 15, 2003, six pages.
Japanese Abstract for Publication No. 2005-119991 published May 12, 2005, 14 pages.
Japanese Abstract for Publication No. 2000-268885 published Sep. 29, 2000, 12 pages.
Grant A. Krafft et al. "Synthesis of 14C-Labeled 10,11-Epoxyfarnesyl Diazoacetate, A Potential Photoaffinity Labeling Reagent for Insect Juvenile Hormone Binding Proteins," Journal for Labelled Compounds and Radiopharmaceuticals, vol. XIX, No. 4, pp. 591-596.
H. Wild et al. "Chain Elongation of Carbohydrates via the C-Phenylglycine Method," Liebigs Ann. Chemical, Apr. 1986, pp. 1548-1567.
Kenichi Mishima et al. "Vitamin E isoforms α-tocotrienol and γ-tocopherol prevent cerebral infarction in mice," Neuroscience Letters 337, 2003, pp. 56-60.
Jiro Takata et al. "Novel d-γ-tocopherol derivative as a prodrug for d-y-tocooherol and a two-step prodrug for S-γ-CEHC," Journal of Lipid Research, vol. 43, 2002, pp. 2196-2204.

* cited by examiner

*Primary Examiner* — Bernard Dentz
(74) *Attorney, Agent, or Firm* — Rankin, Hill & Clark LLP

(57) ABSTRACT

It is intended to provide a drug which is efficacious in treating and preventing diseases wherein ischemia or an inflammatory substance associated with ischemia participates in the onset or worsening thereof. Because of containing as the active ingredient a substance selected from among farnesol, a farnesol derivative, a tocopherol derivative, a tocotrienol derivative, pharmacologically acceptable salts thereof and solvates thereof, the above-described inhibitor of ischemic disorders can exert therapeutic and preventive effects on diseases wherein ischemia or an inflammatory substance associated with ischemia participates in the onset or worsening thereof (for example, brain infarction, brain edema, cardiac infarction, etc.) not only by the administration in the acute ischemic stage but also by the therapeutic administration in subacute and/or chronic stages after ischemia-reperfusion. It is also intended to provide a farnesol carboxylic acid ester derivative and a method of producing the same.

6 Claims, 8 Drawing Sheets

FIG. 1

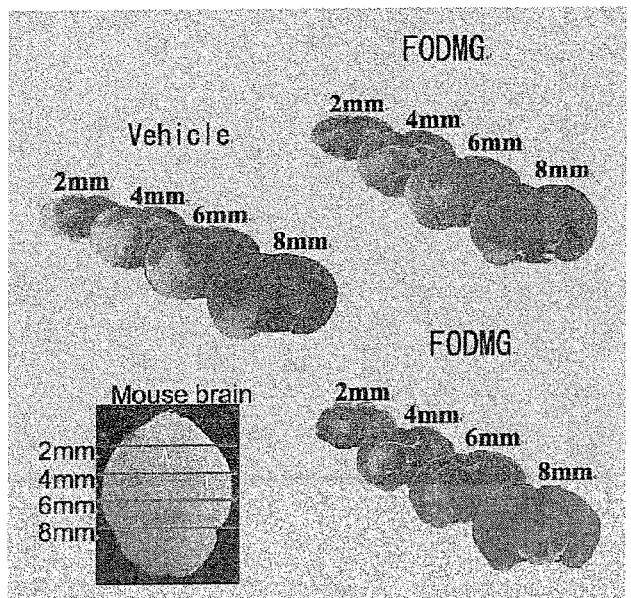

brain slice samples of MCA-occluded mice 24 hours after occlusion

FIG. 2

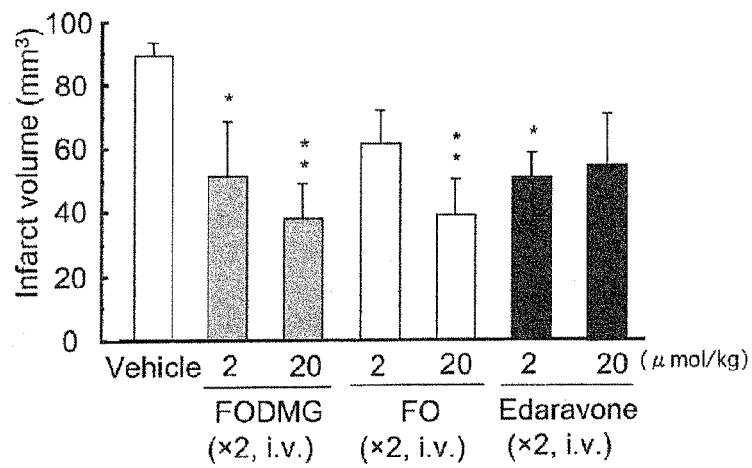

*P<0.05, **P<0.01 compared with Vehicle, Dunnett test

Preventive effect of FODMG on ischemia-reperfusion damage:
Preventive effects of FO and FODMG against the infarct
volume induced by MCA occlusion in ddY mice. Drugs were administered at 0 hr and 3 hr
from start time of the MCA occlusion. FO was dissolved in DMSO. FODMG was dissolved in
water. *P<0.05, **P<0.01 compared with vehicle, Dunnett test.

Curative effect of FODMG on ischemia-reperfusion damage:
Curative effects of FODMG against the
infarct volume induced by MCA occlusion in ddY mice. Drugs were administered at 6 hr
and/or 10 hr after MCA occlusion. FODMG was dissolved water.   *P<0.05, **P<0.01
compared with vehicle, Dunnett test.

FIG. 5

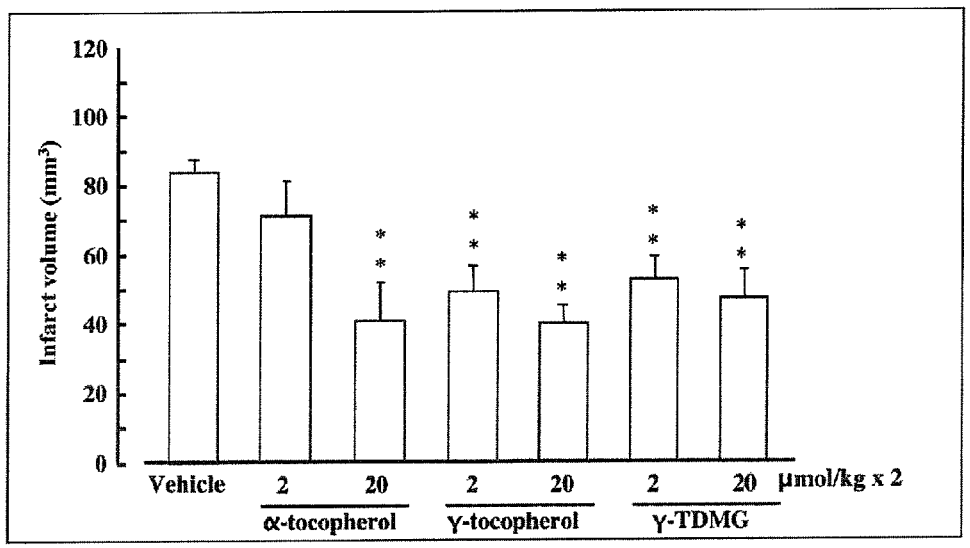

Preventive effect of γ-TDMG on ischemia-reperfusion damage:
Preventive effects of α-Toc, γ-Toc, and γ-TDMG
against the infarct volume induced by MCA occlusion in ddY mice. Drugs were administered
at 0 hr and 3 hr from start time of the MCA occlusion. α-Tocopherol and γ-Tocopherol were
dissolved in DMSO. γ-TDMG was dissolved in water containing 15% propyleneglycol.
*$P<0.05$, **$P<0.01$ compared with vehicle, Dunnett test.

Curative effect of γ-TDMG on ischemia-reperfusion damage:
Curative effects of γ-Toc and γ-TDMG against the
infarct volume induced by MCA occlusion in ddY mice. Drugs were administered at 6 hr after
the MCA occlusion. γ-Toc were dissolved in DMSO. γ-TDMG was dissolved in water
containing 15% propyleneglycol. *$P<0.05$, **$P<0.01$ compared with vehicle, Dunnett test.

FIG. 7

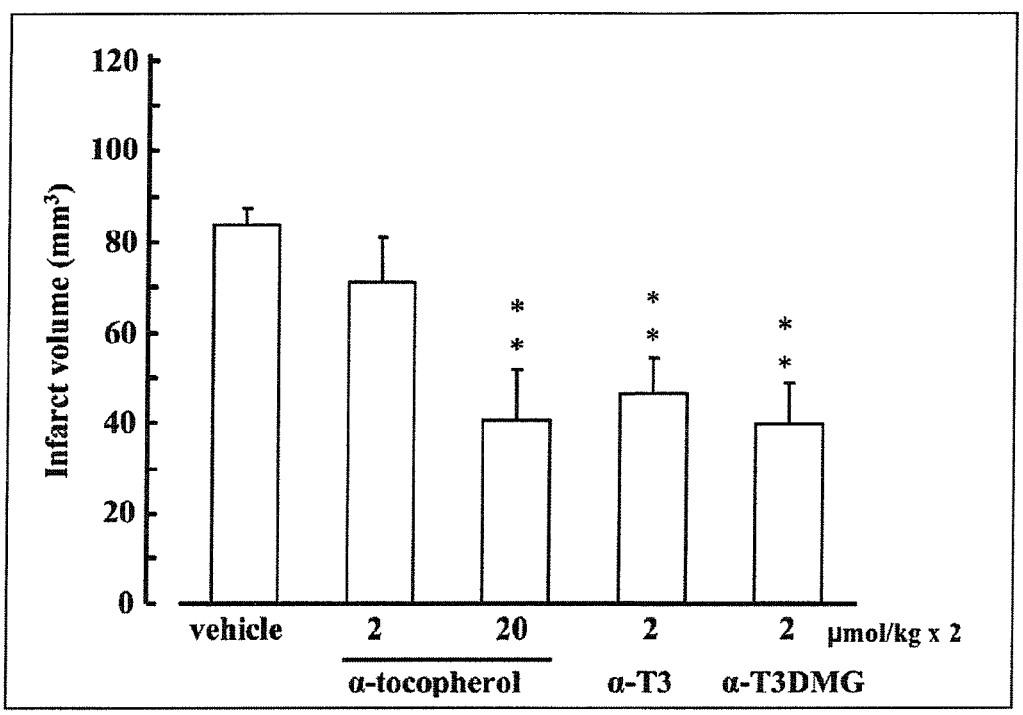

Preventive effect of α-T3DMG on ischemia-reperfusion damage:
Preventive effects of α-tocopherol, α-T3, and
α-T3DMG against the infarct volume induced by MCA occlusion in ddY mice. Drugs were administered at 0 hr and 3 hr from start time of the MCA occlusion. α-Tocopherol and α-T3 were dissolved in DMSO. α-T3DMG was dissolved in water containing 15% propyleneglycol.
*$P<0.05$, **$P<0.01$ compared with vehicle, Dunnett test.

Curative effect of α-T3DMG on ischemia-reperfusion damage:
Curative effects of α-Tocopherol and α-T3DMG
against the infarct volume induced by MCA occlusion in ddY mice. Drugs were administered
at 6 hr after the MCA occlusion. α-Tocopherol was dissolved in DMSO. α-T3DMG was
dissolved in water containing 15% propyleneglycol. *$P<0.05$, **$P<0.01$ compared with
vehicle, Dunnett test.

Preventive effect of γ-TPS on ischemia-reperfusion damage:
Preventive effects of γ-TPS against the infarct volume
induced by MCA occlusion in ddY mice. Drugs were administered at 0 hr and 3 hr from start
time of the MCA occlusion. γ-TPS was dissolved in water. *$P<0.05$, **$P<0.01$ compared with
vehicle, Dunnett test.

Curative effect of γ-TPS on ischemia-reperfusion damage:
Curative effects of γ-TPS against the infarct volume
induced by MCA occlusion in ddY mice. Drugs were administered at 6 hr after the MCA
occlusion. γ-TPS was dissolved in water. *P<0.05, **P<0.01 compared with vehicle, Dunnett
test.

INHIBITOR OF ISCHEMIC DISORDERS

RELATED APPLICATIONS

This application claims the priority of Japanese Patent Application No. 2007-225021 filed on Aug. 31, 2007, which is incorporated herein by reference.

FIELD OF THE INVENTION

The present invention relates to the pharmaceuticals useful for the treatment and prevention of the diseases wherein in vivo ischemia or an inflammatory substance associated with ischemia is involved in the onset or worsening thereof.

BACKGROUND OF THE INVENTION

In recent years, ischemic cerebrovascular disorders (cerebral infarction, cerebral edema, cerebral hemorrhage, cerebral contusion, neonatal hypoxic-ischemic encephalopathy), neurodegenerative diseases (Parkinson's disease, Alzheimer's disease), lung diseases (pulmonary oxygen intoxication, adult respiratory distress syndrome), ischemic heart diseases (angina, myocardial infarction, etc.), cardiovascular diseases (arteriosclerosis), gastrointestinal diseases (peptic ulcer, ulcerative colitis, Crohn's disease), etc., the conditions and diseases wherein ischemia and an inflammatory substance associated with ischemia is considered to be involved in the onset or worsening thereof are wide-ranging and too numerous to mention. Most of these diseases are progressive, and the development of the preventive agent and therapeutic agent is strongly awaited.

Ischemic cerebrovascular disorders, in particular cerebral infarction, are progressive diseases wherein various mechanisms of disorders take place in a domino fashion, because of a decrease in the cerebral blood flow, and the brain damage spreads from the ischemic core to the periphery. Although the prevention of damage in the acute stage is certainly important, the treatment in the subacute and chronic stages after the onset of the disease is very important in view of the seriousness and QOL. Therapeutic agents usable after the onset of cerebral infarction are very scarce; in particular there are no practical therapeutic drugs for the subacute and chronic stages after the onset of the disease. At present, there are thrombolytic agents such as tissue plasminogen activator (tPA) and hydroxy radical scavengers such as edaravone as the therapeutic drugs for acute stage cerebral infarction to improve the ischemic core due to decreased cerebral blood flow. However, they have problems of serious side effects such as bleeding and renal failure. Thus, the development of an excellent therapeutic drug for the ischemic cerebrovascular disorder in the subacute or chronic stage is expected, which can afford the time up to the start of application after the onset of cerebral infarction.

The inventors have disclosed that, when vitamin E homologs were intravenously administered to the mouse middle cerebral artery (MCA) occlusion model twice, immediately before infarction and during infarction, for prophylactic administration, 2R-γ-tocopherol (γ-Toc) and 2R-α-tocotrienol (α-T3) exhibited an excellent infarct inhibitory effect, and therefore have a preventive effect in vivo on the cerebral infarction damage in the acute stage (Non-patent literature 1).

Vitamin E homologs are each insoluble in water and cannot be administered intravenously so that no rapid bioavailability can be secured. Thus, experiments have been attempted to intravenously administer them by making them soluble with an organic solvent such as dimethyl sulfoxide (DMSO) or a surfactant. However, the solubilization with such an organic solvent is not clinically suitable and the use of a large amount of a nonionic surfactant may cause a serious problem such as anaphylactic shock. The use of them cannot eliminate harmful effects completely when administered repeatedly.

The inventors have disclosed that a specific tocopherol derivative (Non-patent literature 2) and a tocotrienol derivative (patent literature 1) were intravenously administrable water-soluble derivative. The sodium salt of tocopheryl phosphate is also known as a water-soluble derivative of tocopherol.

However, there have been so far no reports regarding the therapeutic effects of vitamin E homologs or the derivatives of vitamin E homologs for ischemia-reperfusion injury by the administration thereof after the infarction (ischemia) reperfusion, i.e., after the onset of infarction, for the therapeutic administration.

In addition, there have been no reports regarding the preventive effect of the derivatives of vitamin E homologs for cerebral infarction injury in the acute stage by intravenous administration thereof both immediately before infarction and during infarction for the prophylactic administration.

On the other hand, farnesol is a kind of sesquiterpene having three isoprene units and it is a colorless liquid contained in the essential oil of rose, lemongrass, and citronella. Farnesol is used as a fragrance and a skin protective agent and is expected to possess excellent pharmaceutical effects such as a preventive effect against hyperlipidemia, an antimicrobial effect against fungi, and a protective effect against oxidative damage.

There have been so far no reports, however, that farnesol and its analogs and their derivatives achieve a therapeutic effect for ischemia-reperfusion injury by the administration thereof after the infarction (ischemia) reperfusion, i.e., after the onset of infarction, for the therapeutic administration. There also have been no reports that they achieve a preventive effect for cerebral infarction injury in the acute stage by intravenous administration thereof both immediately before infarction and during infarction for the prophylactic administration.

In addition, farnesol is a totally water-insoluble and volatile compound. Therefore, the solubilization method by the addition of a large amount of nonionic surfactant is investigated for the preparation of a water-soluble drug or water-based cosmetics of farnesol. The use of a large amount of surfactant may cause a serious problem such as anaphylactic shock.

Thus, a farnesol derivative which has a high melting point, is solid at room temperature, has a high water-solubility, and is capable to provide a useful in vivo action has also been in demand.

PATENT LITERATURE 1: Japanese Patent Application No. 2000-268885

NON-PATENT LITERATURE 1: Mishima K, Tanaka T, Pu F, Egashira N, Iwasaki K, Hidaka R, Matsunaga K, Takata J, Karube Y, Fujiwara M. Vitamin E isoforms α-tocotrienol and γ-tocopherol prevent cerebral infarction in mice. Neuroscience Let 2003; 337:56-60.

NON-PATENT LITERATURE 2: Takata J., Hidaka R., Yamasaki A., Hattori A., Fukushima T., Tanabe M., Matsunaga K., Karube Y., Imai K., Novel d-γ-tocopherol derivative as a prodrug for d-γ-tocopherol and a two-step prodrug for S-γ-CEHC. J. Lipid Res., 43, 2196-2204 (2002).

DISCLOSURE OF THE INVENTION

The present invention was made in view of the conventional art and has an object to provide pharmaceuticals effective for the treatment and prevention of diseases wherein ischemia or an inflammatory substance associated with ischemia is involved in the onset or worsening thereof.

As a result of extensive studies by the present inventors in order to solve the above described problems, they have found that a specific farnesol carboxylic acid derivative has a high melting point, is solid at room temperature, has an excellent water-solubility, and is capable to provide a useful in vivo action of farnesol. They also have found that farnesol and the farnesol derivative can achieve the desired objective as a therapeutic agent and a preventive agent for the diseases wherein ischemia or an inflammatory substance associated with ischemia is involved in the onset or worsening thereof.

In addition, the present inventors have found that a specific tocopherol derivative and a specific tocotrienol derivative can also achieve the desired objective as a therapeutic agent and a preventive agent for the diseases wherein ischemia or an inflammatory substance associated with ischemia is involved in the onset or worsening thereof. The present invention has been completed on the basis of the above findings.

The present invention provides a farnesol carboxylic acid ester derivative represented by formula (1):

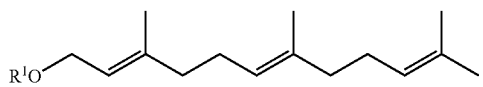

(1)

wherein $R^1$ represents a carboxylic acid residue having a nitrogen substituent selected from the group consisting of an amino acid residue, an N-acyl amino acid residue, an N-alkyl amino acid residue, an N,N-dialkylamino acid residue, a pyridinecarboxylic acid residue, and a physiologically acceptable salt thereof selected from a hydrohalic acid salt, an alkylsulfonic acid salt, and an acidic sugar salt.

The present invention also provides an inhibitor of ischemia-reperfusion disorder, comprising, as an active ingredient, at least one substance selected from the group consisting of farnesol, a farnesol derivative, a pharmacologically acceptable salt thereof, a solvate thereof and a hydrate thereof, wherein said farnesol and farnesol derivative are represented by formula (2):

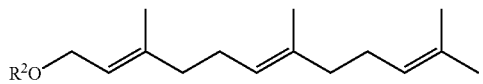

(2)

wherein $R^2$ represents a hydrogen atom or a carboxylic acid residue having a nitrogen substituent selected from the group consisting of an amino acid residue, an N-acyl amino acid residue, an N-alkyl amino acid residue, an N,N-dialkylamino acid residue, a pyridinecarboxylic acid residue, and a physiologically acceptable salt thereof selected from a hydrohalic acid salt, an alkylsulfonic acid salt, and an acidic sugar salt.

The farnesol derivatives represented by said formula (1) or (2) may include a trans form and a cis form for the hydrogen atom at 2-position and the methyl group at 3-position of the farnesyl group ($-[CH_2CH=CH(CH_3)CH_2]_3-H$), and a trans form and a cis form for the hydrogen atom at 6-position and the methyl group at 7-position. In the present invention, these isomers (i.e., (2E,6E), (2E,6Z), (2Z,6E), (2Z,6Z), and their mixtures) may also been included.

In addition, the present invention provides an inhibitor of ischemia-reperfusion disorder, comprising, as an active ingredient, at least one substance selected from the group consisting of a tocopherol derivative or a tocotrienol derivative, a pharmacologically acceptable salt thereof, a solvate thereof and a hydrate thereof, wherein said tocopherol derivative and tocotrienol derivative are represented by formula (3):

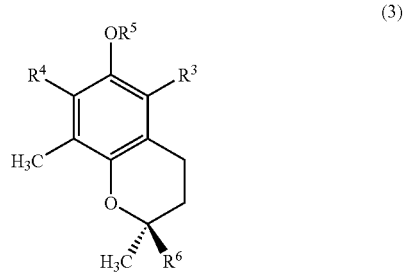

(3)

wherein $R^3$ and $R^4$ represent a hydrogen atom or a methyl group, respectively;

$R^5$ represents a carboxylic acid residue having a nitrogen substituent or a phosphoric acid residue, wherein said carboxylic acid residue having the nitrogen substituent is selected from the group consisting of an amino acid residue, an N-acyl amino acid residue, an N-alkyl amino acid residue, an N,N-dialkylamino acid residue, a pyridinecarboxylic acid residue, and a physiologically acceptable salt thereof selected from a hydrohalic acid salt, an alkylsulfonic acid salt, and an acidic sugar salt, and wherein said phosphoric acid residue is represented by $PO(OR^7)_2$, in which the group $R^7$ is either identical to or different from each other and selected from the group consisting of a hydrogen atom, a methyl group, a physiologically acceptable alkali metal and a physiologically acceptable alkaline earth metal; and $R^6$ is a group represented by formula (3a) or (3b):

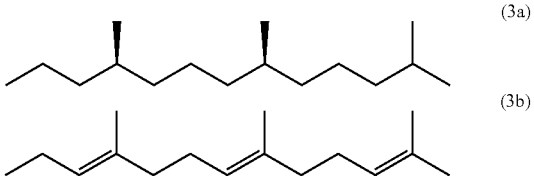

The tocopherol/tocotrienol ester derivative represented by said formula (3) may include a trans form and a cis form for the hydrogen atom at 2-position and the methyl group at 3-position of the farnesyl group of the group (3b), and a trans form and a cis form for the hydrogen atom at 6-position and the methyl group at 7-position; the present invention may also include these isomers.

The therapeutic or preventive agent of cerebral infarction, cerebral edema, or myocardial infarction of the present invention is characterized by containing, as an active ingredient, at least one substance selected from the group consisting of: farnesol, the farnesol derivative, the tocopherol derivative, and the tocotrienol derivative according to any of said formulas (1) to (3); pharmacologically acceptable salts thereof; solvates thereof; and hydrates thereof.

The production method of the farnesol carboxylic acid ester derivative to be provided by the present invention is characterized by protecting a primary or secondary amino group of an amino acid or a hydroxyl group or a thiol group as a side chain of an amino acid with a protecting group and esterifying the protected amino acid with farnesol.

Another production method of the farnesol carboxylic acid ester derivative provided by the present invention is characterized by esterifying farnesol with a hydrohalic acid salt of an N,N-dialkylamino acid in the presence of an active esterifying reagent.

The inhibitor of ischemic disorders of the present invention containing, as an active ingredient, a substance selected from the group consisting of farnesol, farnesol derivatives, tocopherol derivatives, tocotrienol derivatives, pharmacologically acceptable salts thereof and solvates thereof, can achieve not only the preventive effect by the administration in the acute ischemic stage, but also the therapeutic effect for the diseases wherein ischemia or an inflammatory substance associated with ischemia is involved in the onset or worsening thereof by the therapeutic administration in subacute and chronic stages after ischemia-reperfusion.

In addition, the farnesol derivatives provided by the present invention can be obtained as a water-soluble solid.

BRIEF DESCRIPTION OF THE DRAWINGS

FIG. 1 illustrates the preventive effect of ischemic brain damage by the farnesol derivative of the present invention.

FIG. 2 illustrates the preventive effect of ischemic brain damage by the farnesol derivative of the present invention.

FIG. 5 illustrates the preventive effect of ischemic brain damage by the tocopherol derivative of the present invention.

FIG. 7 illustrates the preventive effect of ischemia-reperfusion brain damage by the tocotrienol derivative of the present invention.

BEST MODE FOR CARRYING OUT THE INVENTION

Figure 3:
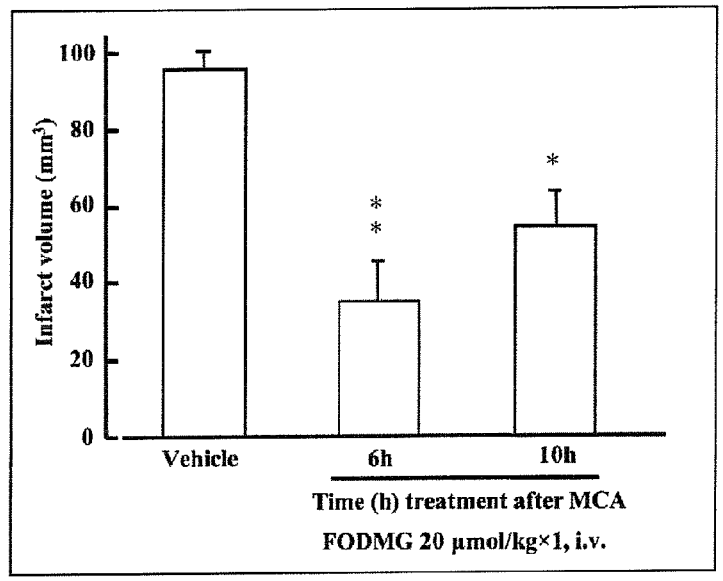
FIG. 3 illustrates the therapeutic effect of ischemic brain damage by the farnesol derivative of the present invention.

Hereinafter, preferable embodiments of the present invention will be described.

The present invention relates to the farnesol carboxylic acid ester derivative represented by the below-described formula (1) and the production method thereof

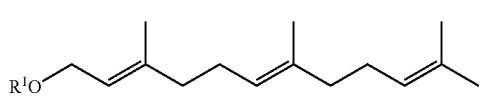

(1)

wherein $R^1$ represents a carboxylic acid residue having a nitrogen substituent selected from the group consisting of an amino acid residue, an N-acyl amino acid residue, an N-alkyl amino acid residue, an N,N-dialkylamino acid residue, a pyridinecarboxylic acid residue, and a physiologically acceptable salt thereof selected from a hydrohalic acid salt, an alkylsulfonic acid salt and an acidic sugar salt.

In the present invention, the term "carboxylic acid residue" means the residue obtained by removing the OH group from the carboxyl group (COOH) of a carboxylic acid.

In the carboxylic acid residue having a nitrogen substituent, the alkyl group of an alkyl-substituted amino group is a linear or branched alkyl group having 1 to 6 carbon atoms. Examples include a methyl group, an ethyl group, an n-propyl group, an n-pentyl group, an n-hexyl group, an isopropyl group, an isobutyl group, a 1-methylpropyl group, a tert-butyl group, a 1-ethylpropyl group, and an isoamyl group, and in particular a methyl group and an ethyl group are preferable. As the acyl group of an acyl-substituted amino group, an acyl group having a linear or branched alkyl group of 1 to 6 carbon atoms as the hydrocarbon chain is preferable, and the specific examples of alkyl groups are as described above.

In addition, the amino group and the carbonyl group are preferably connected by a linear, branched, or cyclic alkylene group having 1 to 6 carbon atoms. The branched alkylene group means an alkylene group derived from the alkyl groups such as an isopropyl group, an isobutyl group, a 1-methylpropyl group, a tert-butyl group, and a 1-ethylpropyl group. The cyclic alkylene group means an alkylene group containing a ring such as a cyclopentane ring, a cyclohexane ring, or a methylcyclohexane ring in the structure. The especially preferable alkylene group is a methylene group or an ethylene group.

The nitrogen substituent in the carboxylic acid residue may form a salt. For example, the hydrochloride, hydrobromide, etc. are preferable as the hydrohalic acid salt. In the present invention, the melting point of the hydrohalic acid salt is higher than that of the original farnesol, and there is the advantage in that the handling is easy in the drug formulation. Examples of alkylsulfonate salts include methanesulfonates. Examples of acidic sugar salts include gluconates, glucoheptanoates, and lactobionates.

The following method is illustrated as the production method of the farnesol carboxylic acid ester derivatives of the present invention.

The esterification of farnesol represented by the below-described formula (4) with a carboxylic acid having a nitrogen substituent, its reactive acid derivative, or the hydrohalic acid salt thereof according to a conventional method may produce the farnesol carboxylic ester (1) of the present invention. The stereoisomerism of a farnesyl group in the formula (4) is as explained in the above-described formula (1).

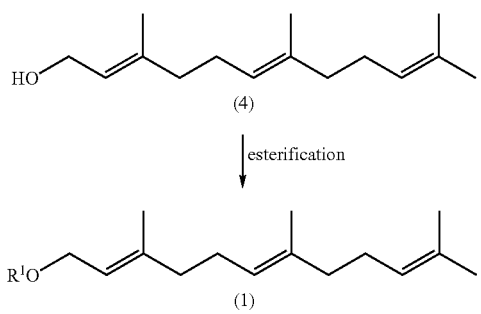

The esterification of farnesol is carried out according to a conventional method. For the esterification of the farnesol with the amino acid having a primary or secondary amino group or having a hydroxyl group or a thiol group in the side chain, it is preferable to protect these primary or secondary amino groups, hydroxyl group, and thiol group with a suitable protecting group such as a tert-butoxycarbonyl group (hereinafter abbreviated as "t-BOC group") and a benzyloxycarbonyl group (hereinafter abbreviated as "Z group").

As for the N,N-dialkylamino acid, it is preferable to use its hydrohalic acid salt and carry out the reaction in the presence of an active esterifying reagent such as dicyclohexylcarbodiimide (hereinafter abbreviated as "DCC") or N,N-disuccinimidooxalate (hereinafter abbreviated as "DSO"). On this occasion, anhydrous pyridine is preferable as the solvent.

In the method wherein a reactive acid derivative is used, it is preferable to use an acid halogenide, in particular an acid chloride. On this occasion, anhydrous benzene-anhydrous pyridine mixture is preferable as the solvent.

Hydrohalic acid salts, alkylsulfonate salts, acidic sugar salts may be produced, according to a conventional method, by the reaction of a free amino acid ester with a hydrohalic acid, an alkylsulfonic acid, or the lactone form of a acidic sugar. In addition, hydrohalic acid salts can be produced, after the production of an N-acyl amino acid ester, by deprotection with a hydrohalic acid according to a conventional method.

The hydrohalic acid salt of farnesol carboxylic ester (1) of the present invention is a crystalline powder with a high melting point, and the handling thereof is easy and simple from the standpoint of view of formulation technology. In addition, it has a high water-solubility. Accordingly, it is useful for intravenously administrable drugs, eye-drops, oral drugs, water-based ointments, sprays, etc.

In addition, the present invention relates to a therapeutic agent or a preventive agent, containing farnesol or a farnesol derivative represented by the below-described formula (2), a salt thereof, or a solvate thereof, for the diseases wherein ischemia or an inflammatory substance associated with ischemia is involved in the onset or worsening thereof. The compound represented by the formula (2) can be added solely into a drug, or its pharmacologically acceptable salt or solvate may be formulated into the drug.

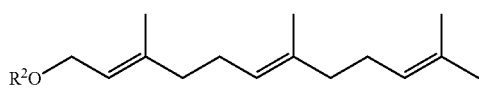

(2)

wherein $R^2$ represents a hydrogen atom or a carboxylic acid residue having a nitrogen substituent selected from the group consisting of an amino acid residue, an N-acyl amino acid residue, an N-alkyl amino acid residue, an N,N-dialkylamino acid residue and a pyridinecarboxylic acid residue, and a physiologically acceptable salt thereof selected from a hydrohalic acid salt, an alkylsulfonic acid salt and an acidic sugar salt.

The carboxylic acid residue $R^2$ having a nitrogen substituent is as explained for the above-described $R^1$.

The present invention also relates to a therapeutic agent or a preventive agent, containing a tocopherol ester derivative or a tocotrienol ester derivative represented by the below-described formula (3), a salt thereof, or a solvate thereof, for the diseases wherein ischemia or an inflammatory substance associated with ischemia is involved in the onset or worsening thereof. The compound represented by the formula (3) can be added solely into a drug, or its pharmacologically acceptable salt or solvate may be formulated into the drug.

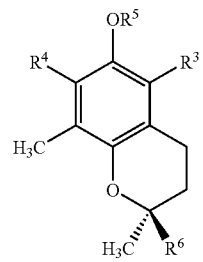

(3)

wherein $R^3$ and $R^4$ represent a hydrogen atom or a methyl group, respectively;

$R^5$ represents a carboxylic acid residue having a nitrogen substituent or a phosphoric acid residue, wherein said carboxylic acid residue having the nitrogen substituent as represented by $R^5$ is selected from the group consisting of an amino acid residue, an N-acyl amino acid residue, an N-alkyl amino acid residue, an N,N-dialkylamino acid residue, a pyridinecarboxylic acid residue, and a physiologically acceptable salt thereof selected from a hydrohalic acid salt, an alkylsulfonic acid salt and an acidic sugar salt, and wherein said phosphoric acid residue is represented by $PO(OR^7)_2$ as represented by the group $R^5$, in which the group $R^7$ is either identical to or different from each other and selected from the group consisting of a hydrogen atom, a methyl group and a physiologically acceptable alkali and alkaline earth metal; and $R^6$ is a group represented by formula (3a) or (3b):

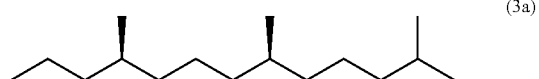

(3a)

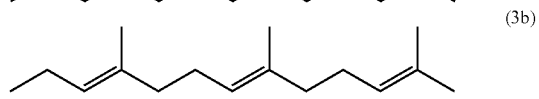

(3b)

Tocotrienol/tocopherol carboxylate wherein $R^5$ is a carboxylic acid residue having a nitrogen substituent can be represented by the below-described formula (3-1).

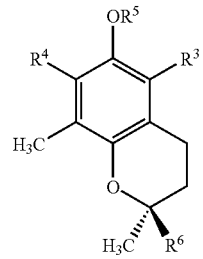

(3-1)

wherein $R^3$, $R^4$, and $R^6$ are as defined in the above-described formula (3), respectively; and $R^5$ is a carboxylic acid residue having a nitrogen substituent.

In the carboxylic acid residue having a nitrogen substituent, the alkyl group of the alkyl-substituted amino group is a linear or branched alkyl group having 1 to 6 carbon atoms. Examples may include a methyl group, an ethyl group, an n-propyl group, an n-pentyl group, an n-hexyl group, an isopropyl group, an isobutyl group, a 1-methylpropyl group, a tert-butyl group, a 1-ethylpropyl group, and an isoamyl group, and a methyl group and an ethyl group are particularly preferable. As the acyl group of an acyl-substituted amino group, an acyl group having a linear or branched alkyl group of 1 to 6 carbon atoms as the hydrocarbon chain is preferable, and the specific examples of alkyl groups are as described above.

In addition, the amino group and the carbonyl group may be preferably connected by a linear, branched, or cyclic alkylene group having 1 to 6 carbon atoms. The branched alkylene group means an alkylene group derived from the alkyl groups such as an isopropyl group, an isobutyl group, a 1-methylpropyl group, a tert-butyl group, and a 1-ethylpropyl group. The cyclic alkylene group means an alkylene group containing a ring such as a cyclopentane ring, a cyclohexane ring, or a methylcyclohexane ring, etc. in the structure. The especially preferable alkylene group is a methylene group or an ethylene group.

The nitrogen substituent in the carboxylic acid residue may form a salt. For example, the hydrochloride, hydrobromide, etc. are preferable as the hydrohalic acid salt. In the present invention, a melting point of the hydrohalic acid salt is higher than that of the original tocopherols and tocotrienols, and there is the advantage in that the handling is easy in the drug formulation. Examples of alkylsulfonate salts may include methanesulfonates. Examples of acidic sugar salts include gluconates, glucoheptanoates, and lactobionates.

Tocotrienol/tocopherol phosphate esters wherein $R^5$ is a phosphoric acid residue can be represented by the below-described formula (3-2).

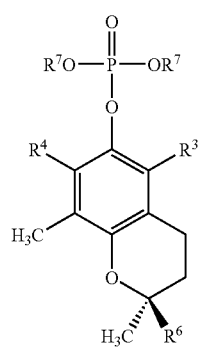

(3-2)

wherein $R^3$, $R^4$, and $R^6$ are as defined in the above-described formula (3), respectively; and $R^7$s are either identical to or different from each other, and they are selected from the group consisting of a hydrogen atom, a methyl group, an alkali metal, and an alkaline earth metal.

The inhibitor of ischemia-reperfusion disorder of the present invention may contain other components within the range that does not impair the effect, in addition to one or more of the compounds represented by the above-described formulas (1) to (3) to be contained as the active ingredient. The drug formulation can be achieved by a known method with the use of additives such as excipient, lubricant, binder, disintegrator, stabilizer, flavor, diluent, surfactant, emulsifier, solubilizer, absorption promoter, humectant, adsorbent, filler, extender, emollient, and preservative as pharmaceutically acceptable carriers. Conventionally known preventive agents or therapeutic agents for ischemic diseases can also be used in combination.

Examples of dosage forms for the ischemia-reperfusion disorder inhibitor of the present invention may include tablets, capsules, granules, powder, pills, and troches; or liquid preparations such as syrup and injections. The liquid preparations may be filled and sealed after by sterilization-filtration with a membrane filter etc., as necessary. Thereafter, they may also be subjected to a widely used sterilization process such as high-pressure steam sterilization or hot water sterilization.

The inhibitor of ischemia-reperfusion disorder according to the present invention may be administered through routes of oral administration, intravenous administration such as intravenous injection, arterial administration such as arterial injection (intracoronary administration, etc.), intramuscular administration such as intramuscular injection, percutaneous administration, nasal administration, intracutaneous administration, subcutaneous administration, intraperitoneal administration, intrarectal administration, mucosal administration, and inhalation. The parenteral administration method such as injection is preferable at least in the acute and sub-acute stages.

Examples of injections may include sterile aqueous or nonaqueous solutions, suspensions, and emulsions. In such injections, one or more active substances and at least one inert aqueous diluent or inert nonaqueous diluent are mixed. As necessary, the additives such as preservative, wetting agent, emulsifier, dispersant, stabilizer, and solubilizer may be further added. These are usually sterilized by filtration (with a bacteria retentive filter, etc.), mixing with disinfectant, or γ-ray irradiation, or after these treatments, they may be converted to a solid composition by freeze-drying etc. and be used by adding sterile water or sterile injection diluent immediately before use.

The ischemia-reperfusion disorder inhibitors of the present invention are useful as a therapeutic agent or a preventive agent for the diseases wherein in vivo ischemia or an inflammatory substance associated with ischemia is involved in the onset or worsening thereof (representative examples including ischemic cerebrovascular disorders such as cerebral infarction and cerebral edema and ischemic heart disease such as myocardial infarction). They can be administered for the patients who need such a treatment or prevention.

The dosage of the active ingredient of the present invention, namely the compound represented by the formulas (1) to (3), is dependent on the route of administration, symptom, age, body weight, etc. They may range normally from 0.01 to 1,000 μmol/kg, preferably from 0.1 to 100 μmol/kg, and be administered once or several times per day.

Example 1

The following is the description regarding examples of the present invention. However, the present invention is not limited by these examples.

It is preferable to prepare the compounds represented by the formula (1) by the production methods A to C as described below.

Production Method A

N,N-dialkylamino acid hydrochloride (3.1 mmol) and DCC (3.1 mmol) are added to 30 mL of anhydrous pyridine. After stirring for 30 minutes, farnesol (3.1 mmol) is added thereto and stirred at room temperature for 16 hours. The solvent is removed under reduced pressure, the residue is suspended in distilled water and the soluble fractions are extracted with ethyl acetate. The extract is dehydrated with anhydrous sodium sulfate, and then the solvent is removed under reduced pressure. The residue is purified by silica gel flash chromatography separation (elution solvent: n-hexane-ethyl acetate) to obtain N,N-dialkylamino acid farnesol ester.

Production Method B

N,N-dialkylamino acid farnesol ester is dissolved in a small amount of acetone. Hydrochloric acid (2 times in moles)-dioxane is added thereto, and the solvent is removed under reduced pressure. The residue is recrystallized from acetone to obtain the hydrochloride of N,N-dialkylamino acid farnesol ester.

Production Method C

Amino acid (0.1 mol) is dissolved in 100 mL of distilled water-dioxane (1:1, v/v), and 30 mL of triethylamine is added thereto. Then, di-tert-butyl Bicarbonate is gradually added to the mixture, and stirred for 30 minutes at room temperature. Dioxane is removed under reduced pressure, and 50 mL of sodium hydrogencarbonate aqueous solution (0.5 M) is added to the residue. The mixture is washed with 100 mL of ethyl acetate, and the ethyl acetate layer is washed with 50 mL of sodium hydrogencarbonate solution. The aqueous layers are combined and adjusted to acidic (pH 3) with a citric acid aqueous solution (0.5 M) under cooling with ice, saturated with sodium chloride, and then extracted with ethyl acetate (100 mL×3 times). The extract is dehydrated with anhydrous sodium sulfate, and the solvent is removed under reduced pressure. A N-t-BOC amino acid is obtained by adding isopropyl ether to the oily residue or by the crystallization thereof under cooling.

Farnesol (5 mmol), the N-t-BOC amino acid (5 mmol), and DCC (5 mmol) are added to 30 mL of anhydrous pyridine, and stirred at room temperature for 20 hours. The solvent is removed under reduced pressure, and ethyl acetate is added to the residue to extract the soluble fractions (100 mL×2 times). The extract is concentrated under reduced pressure, and the residue is purified by silica gel column chromatography separation (elution solvent: n-hexane-ethyl acetate) to obtain a farnesol N-t-BOC-amino acid ester.

The Farnesol N-t-BOC-amino acid ester is dissolved in a small amount of acetone, and hydrochloric acid-dioxane (2.5 to 4.0 N) is added thereto so that the amount of hydrochloric acid is 20 times of the ester in moles. After stirring for 1 hour, the solvent is removed under reduced pressure. The residue is recrystallized from acetone-methanol mixture or ethyl acetate-methanol mixture to obtain the hydrochloride of the farnesol amino acid ester.

The hydrochloride of the farnesol amino acid ester (3 mmol) is added to 150 mL of water, the solution is adjusted to pH 7 to 8 with sodium hydrogencarbonate and then extracted with ethyl acetate (100 mL×3 times). The extract is dehydrated with anhydrous sodium sulfate, and the solvent was removed under reduced pressure to obtain the farnesol amino acid ester as an oil.

It is preferable to synthesize the compounds represented by the formula (3-1) by any of the below-described production methods D to G.

Production Method D

Amino acid (0.1 mol) is dissolved in 100 mL of distilled water-dioxane (1:1, v/v), and 30 mL of triethylamine is added thereto. Then, di-tert-butyl dicarbonate is gradually added to the mixture, and stirred for 30 minutes at room temperature. Dioxane is removed under reduced pressure, and 50 mL of sodium hydrogencarbonate aqueous solution (0.5 M) is added to the residue. The mixture is washed with 100 mL of ethyl acetate, and the ethyl acetate layer is washed with 50 mL of sodium hydrogencarbonate solution. The aqueous layers are combined and adjusted to acidic (pH 3) with a citric acid aqueous solution (0.5 M) under cooling with ice, saturated with sodium chloride, and then extracted with ethyl acetate (100 mL×3 times). The extract is dehydrated with anhydrous sodium sulfate, and the solvent is removed under reduced pressure. A N-t-BOC amino acid is obtained by adding isopropyl ether to the oily residue or by the crystallization under cooling.

Under an argon gas atmosphere, tocopherol or tocotrienol (5 mmol), the N-t-BOC amino acid (5 mmol), and DCC (5 mmol) are added to 30 mL of anhydrous pyridine, and stirred at room temperature for 20 hours. The solvent is removed under reduced pressure, ethyl acetate is added to the residue to extract the soluble fractions (100 mL×2 times). The extract is concentrated under reduced pressure, and the residue is purified by silica gel column chromatography separation (elution solvent: n-hexane-ethyl acetate) to obtain farnesol N-t-BOC-amino acid ester or a tocopherol N-t-BOC-amino acid ester or a tocotrienol N-t-BOC-amino acid ester.

The tocopherol N-t-BOC-amino acid ester or the tocotrienol N-t-BOC-amino acid ester is dissolved in a small amount of acetone, and hydrochloric acid-dioxane (2.5 to 4.0 N) is added thereto so that the amount of hydrochloric acid is 20 times of the ester in moles. After stirring for 1 hour, the solvent is removed under reduced pressure. The residue is recrystallized from acetone-methanol mixture or ethyl acetate-methanol mixture to obtain the hydrochloride of the tocopherol amino acid ester or the tocotrienol amino acid ester.

Production Method E

The hydrochloride of the tocopherol amino acid ester or the tocotrienol amino acid ester (3 mmol) is added to 150 mL of water, and the solution is adjusted to pH 7 to 8 with sodium hydrogencarbonate and then extracted with ethyl acetate (100 mL×3 times). The extract is dehydrated with anhydrous sodium sulfate, and the solvent is removed under reduced pressure to obtain the tocopherol amino acid ester or the tocotrienol amino acid ester as an oil.

Production Method F

Under an argon gas atmosphere, tocopherol or tocotrienol (5 mmol), a N,N-dialkylamino acid hydrochloride (5 mmol), and DCC (5 mmol) are added to 30 mL of anhydrous pyridine, and stirred room temperature for 20 hours. The solvent is removed under reduced pressure, and the residue is suspended in distilled water, adjusted to pH 7 to 8 with sodium hydrogencarbonate, and then extracted with ethyl acetate (100 mL×3 times). The extract is dehydrated with anhydrous sodium sulfate, and the solvent is removed under reduced pressure. The residue is purified by silica gel column chromatography separation (elution solvent: n-hexane-ethyl acetate, 8:2) to obtain a tocopherol N,N-dialkylamino acid ester or a tocotrienol N,N-dialkylamino acid ester.

Production Method G

A tocopherol amino acid ester, a tocotrienol amino acid ester, a tocopherol N,N-dialkylamino acid ester, or a tocotrienol N,N-dialkylamino acid ester (2 mmol) is dissolved in 20 mL of acetone. Hydrochloric acid-dioxane (2.5 to 4.0 N) is added thereto so that the amount of hydrochloric acid is 10 times of the ester in moles, or alkylsulfonic acid (2 mmol) is added. The solvent is removed under reduced pressure, and the residue is recrystallized from acetone-methanol mixture or ethyl acetate-methanol mixture to obtain the hydrochloride or alkylsulfonate salt of the tocopherol amino acid ester, the tocotrienol amino acid ester, the tocopherol N,N-dialkylamino acid ester, or the tocotrienol N,N-dialkylamino acid ester.

It is preferable to synthesize the compounds represented by the formula (3-2) by any of the below-described production methods H to I.

Production Method H

To a mixed solution of 50 mL of t-butyl methyl ether and 5 mL of anhydrous pyridine, 5 g of tocopherol or tocotrienol is dissolved, and 3.68 g of phosphoryl chloride ($POCl_3$) is added little by little with stirring. Under cooling with ice, 20 mL of 15% sulfuric acid aqueous solution is added to separate the layers. To the t-butyl methyl ether layer, 20 mL of 35% sulfuric acid aqueous solution is added, and the mixture is refluxed at 70° C. for 7 hours with stirring. The t-butyl methyl ether layer and the aqueous layer are separated, and the t-butyl methyl ether layer is washed with 100 mL of distilled water three times. The volume of the t-butyl methyl ether layer is adjusted to 200 mL by addition of t-butyl methyl ether. While measuring the pH, 5% sodium hydroxide methanol solution is added to the t-butyl methyl ether layer to adjust the pH to 8.9. The mixture is concentrated under reduced pressure, and acetone is added to the residue to produce a precipitate. The precipitate is dried and washed with methanol to obtain the sodium salt of tocopheryl phosphate or the sodium salt of tocotrienyl phosphate.

Production Method I

To a mixed solution of 50 mL of t-butyl methyl ether and 5 mL of anhydrous pyridine, 5 g of tocopherol or tocotrienol is dissolved, and 3.68 g of phosphoryl chloride ($POCl_3$) is added little by little with stirring. After addition of 20 mL of methanol under cooling with ice, the reaction mixture is purified by silica gel column chromatography separation (elution solvent: n-hexane-ethyl acetate, 8:2) to obtain tocopherol methylphosphoric acid ester or tocotrienol methylphosphoric acid ester.

TABLE 1

| Compound No. | $R^1$ | Compound Name | Salt | Apperance | m.p.(° C.) | Method |
|---|---|---|---|---|---|---|
| 1 | (2E,6E) $(CH_3)_2NCH_2CO-$ | farnesol N,N-dimethylglycinate hydrochloride | HCl | white crystalline | 85-88 | A, B |
| 2 | (2Z/E,6Z/E) $(CH_3)_2NCH_2CO-$ | farnesol N,N-dimethylglycinate hydrochloride | HCl | white crystalline | 90-92 | A, B |
| 3 | (2E,6E) $CH_3NHCH_2CO-$ | farnesol sarcosinate hydrochloride | HCl | white crystalline | 55-60 | C |
| 4 | (2E,6E) $NH_2CH_2CO-$ | farnesol glycinate hydrochloride | HCl | — | — | C |
| 5 | (2E,6E) $(CH_3)_2NCH_2CH_2CO-$ | farnesol N,N-dimethyl-β-alaninate hydrochloride | HCl | — | — | A, B |
| 6 | (2E,6E) $(CH_3CH_2)_2NCH_2CH_2CO-$ | farnesol N,N-diethyl-β-alaninate hydrochloride | HCl | — | — | A, B |

TABLE 2

| Compound No. | MS* (FAB − MS) | $^1$H-NMR spectrum (δ) |
|---|---|---|
| 1 | 308 (M − HCl + H$^+$) | (In $CD_3OD$) 5.39(1H, m), 5.09(2H, m), 4.80(2H, d), 4.14(2H, s), 2.97(6H, s), 2.14-2.05(6H, m), 1.98(2H, m), 1.75(3H, s), 1.66(3H, s), 1.60(6H, s) |
| 2 | 308 (M − HCl + H$^+$) | (In $CD_3OD$) 5.39(1H, m), 5.09(2H, m), 4.80(2H, d), 4.14(2H, s), 2.97(6H, s), 2.12-2.06(6H, m), 1.98(2H, m), 1.75(3H, s), 1.66(3H, s), 1.60(6H, s) |
| 3 | 294 (M − HCl + H$^+$) | (In $CDCl_3$) 9.82(2H, s), 5.36(1H, m), 5.10(2H, m), 4.75(2H, d), 3.85(2H, s), 2.84(3H, s), 2.15-1.98 (8H, m) 1.71(3H, s), 1.69(3H, s), 1.60(3H, s) |
| 4 | 280 (M − HCl + H$^+$) | (In $CDCl_3$) 8.55(3H, s), 5.33(1H, m), 5.10(2H, m), 4.72(2H, d), 3.98(2H, s), 2.12-1.97 (8H, m), 1.70(3H, s 1.60(3H, s), 1.56(3H, s) |
| 5 | 322 (M − HCl + H$^+$) | (In $CDCl_3$) 12.36(1H, s), 5.32(1H, m), 5.10(2H, m), 4.64(2H, d), 4.12(2H, m), 3.38(2H, m), 2.83(6H, s), 2.13-1.96 (8H, m), 1.71(3H, s), 1.68(3H, s), 1.60(3H, s) |
| 6 | 350 (M − HCl + H$^+$) | (In $CDCl_3$) 12.31(1H, s), 5.33(1H, m), 5.11(2H, m), 4.63(2H, d), 3.32(2H, m), 3.17-3.02(6H, s), 2.13-1.96 (8H, m), 1.71(3H, s), 1.68(3H, s), 1.60(3H, s), 1.41(6H, m) |

*mass spectrometry

TABLE 3

| Compound No. | $R^1$ | Compound Name | MS*(FAB − MS) | Apperance | Method |
|---|---|---|---|---|---|
| 7 | (2E,6E) $(CH_3)_2NCH_2CO-$ | farnesol N,N-dimethylglycinate | 308 (M + H$^+$) | oil | A |
| 8 | (2Z/E,6Z/E) $(CH_3)_2NCH_2CO-$ | farnesol N,N-dimethylglycinate | 308 (M + H$^+$) | oil | A |
| 9 | (2E,6E) N-t-BOC-N($CH_3$)$CH_2CO-$ | farnesol N-t-BOC-sarcosinate | 392 (M − H$^−$) | oil | C |
| 10 | (2E,6E) N-t-BOC-$NHCH_2CO-$ | farnesol N-t-BOC-glycinate | 378 (M − H$^−$) | oil | C |
| 11 | (2E,6E) $CH_3NHCH_2CO-$ | farnesol sarcosinate | 294 (M + H$^+$) | oil | C |
| 12 | (2E,6E) $NH_2CH_2CO-$ | farnesol glycinate | 280 (M + H$^+$) | oil | C |

TABLE 3-continued

| Compound No. | R¹ | Compound Name | MS*(FAB − MS) | Apperance | Method |
|---|---|---|---|---|---|
| 13 | (2E,6E)(CH₃)₂NCH₂CH₂CO— | farnesol N,N-dimethyl-β-alaninate | 322 (M + H⁺) | oil | A |
| 14 | (2E,6E)(CH₃CH₂)₂NCH₂CH₂CO— | farnesol N,N-diethyl-β-alaninate | 350 (+H⁺) | oil | A |

*mass spectrometry

TABLE 4

| Comp. No. | Compound name | R³ | R⁴ | R⁵ | Salt | Appearance | m.p. (° C.) | Method |
|---|---|---|---|---|---|---|---|---|
| 15 | 2R-α-tocotrienyl glycinate hydrochloride | CH₃ | CH₃ | NH₂CH₂CO— | HCl | white crystalline | 167-173 | D, G |
| 16 | 2R-α-tocotrienyl sarcosinate hydrochloride | CH₃ | CH₃ | CH₃NHCH₂CO— | HCl | white crystalline | 170-173 | D, G |
| 17 | 2R-γ-tocotrienyl glycinate hydrochloride | H | CH₃ | NH₂CH₂CO— | HCl | white crystalline | 195-198 | D, G |
| 18 | 2R-γ-tocotrienyl sarcosinate hydrochloride | H | CH₃ | CH₃NHCH₂CO— | HCl | white crystalline | 130-132 | D, G |
| 19 | 2R-α-tocotrienyl N,N-dimethyl-glycinate hydrochloride | CH₃ | CH₃ | (CH₃)₂NHCH₂CO— | HCl | white crystalline | 186-188 | F, G |
| 20 | 2R-γ-tocotrienyl N,N-dimethyl-glycinate hydrochloride | H | CH₃ | (CH₃)₂NHCH₂CO— | HCl | white crystalline | 160-161 | F, G |
| 21 | 2R-δ-tocotrienyl N,N-dimethyl-glycinate hydrochloride | H | H | (CH₃)₂NHCH₂CO— | HCl | white solid | unmeasured due to hygroscopicity | F, G |
| 22 | 2R-γ-tocopheryl N,N-dimethyl-glycinate hydrochloride | H | CH₃ | (CH₃)₂NHCH₂CO— | HCl | white crystalline | 161-163 | F, G |

TABLE 5

| No. | Mass spectrometry (m/z, FAB − MS) | ¹H-NMR spectrum (δ ppm, internal standard TMS) |
|---|---|---|
| 15 | 482 (M − HCl + H⁺) | (in CDCl₃) 8.76 (2H, s), 5.09 (3H, m), 4.09 (2H, s), 2.50 (2H, t), 2.11-1.89 (19H, m, including 2.02 (3H, s), 1.92 (3H, s), 1.89 (3H, s)), 1.74-1.47 (16H, m, including 1.67 (3H, s), 1.59 (6H, s), 1.55 (3H, s)), 1.27 (3H, s) |
| 16 | 496 (M − HCl + H⁺) | (in CDCl₃) 9.95 (1H, s), 5.10 (3H, m), 4.09 (2H, s), 2.80 (3H, s), 2.56 (2H, t), 2.12-1.97 (19H, m, including 2.07 (3H, s), 2.00 (3H, s), 1.97 (3H, s)), 1.78-1.52 (16H, m, including 1.67 (3H, s), 1.59 (6H, s), 1.56 (3H, s)), 1.27 (3H, s) |
| 17 | 468 (M − HCl + H⁺) | (in CDCl₃) 8.67 (2H, s), 6.61 (1H, s), 5.10 (3H, m), 4.04 (2H, s), 2.60 (2H, m), 2.16-1.92 (16H, m, including 2.02 (3H, s), 1.92 (3H, s)), 1.69-1.49 (16H, m, including 1.67 (3H, s), 1.58 (6H, s), 1.55 (3H, s)), 1.24 (3H, s) |
| 18 | 482 (M − HCl + H⁺) | (in CDCl₃) 10.01 (1H, s), 6.66 (1H, s), 5.11 (3H, m), 4.04 (2H, s), 2.81 (3H, s), 2.66 (2H, m), 2.10-1.95 (16H, m including 2.08 (3H, s), 2.01 (3H, s)), 1.69-1.49 (16H, m, including 1.67 (3H, s), 1.59 (6H, s), 1.56 (3H, s)), 1.24 (3H, s) |
| 19 | 510 (M − HCl + H⁺) | (in CD₃OD) 5.10 (3H, m), 4.60 (2H, s), 3.06 (6H, s), 2.64 (2H, t), 2.15-1.93 (19H, m, including 2.11 (3H, s), 2.04 (3H, s), 2.01 (3H, s)), 1.85-1.54 (16H, m, including 1.65 (3H, s), 1.58 (6H, s), 1.56 (3H, s)), 1.27 (3H, s) |
| 20 | 496 (M − HCl + H⁺) | (in CDCl₃) 6.63 (1H, s), 5.10 (3H, m) 4.21 (2H, s), 3.09 (6H, s), 2.72 (2H, m), 2.13-1.95 (16H, m, including 2.12 (3H, s), 2.02 (3H, s)), 1.81-1.59 (16H, m, including 1.68 (3H, s), 1.60 (6H, s), 1.59 (3H, s)), 1.28 (3H, s) |
| 21 | 482 (M − HCl + H⁺) | (in CDCl₃) 6.73 (1H, s), 6.69, (1H, s), 5.12 (3H, m) 4.15 (2H, s), 3.08 (6H, s), 2.74 (2H, m), 2.16-1.90 (13H, m, including 2.16 (3H, s)), 1.86-1.52 (16H, m, including 1.67 (3H, s), 1.60 (6H, s), 1.56 (3H, s)), 1.28 (3H, s) |
| 22 | 501 (M − HCl⁺) | (in CDCl₃) 6.63 (1H, s, 5-H), 2.71 (2H, m, 4-H₂), 2.11 (3H, s, 7-CH₃), 2.02 (3H, s, 8-CH₃), 1.76, (2H, m, 3-CH₂), 1.59-1.02 (24H, m, including 1.26 (3H, s, 2-CH₃)), 0.87-0.83 (12H, m). 4.21 (2H, s, NCH₂CO), 3.09 (6H, s, (CH₃)₂N) |

TABLE 6

| Comp. No. | Compound name | $R^3$ | $R^4$ | $R^5$ | Appearance | Mass spectrometry (FAB-MS) | Method |
|---|---|---|---|---|---|---|---|
| 23 | d-α-tocotrienyl N-t-Boc-glycinate | $CH_3$ | $CH_3$ | N-t-BOC-NHCH$_2$CO— | oil | 582 (M + H$^+$) | D |
| 24 | d-α-tocotrienyl N-t-Boc-N-sarcosinate | $CH_3$ | $CH_3$ | N-t-BOC-N(CH$_3$)CH$_2$CO— | oil | 596 (M + H$^+$) | D |
| 25 | d-γ-tocotrienyl N-t-Boc-glycinate | H | $CH_3$ | N-t-BOC-NHCH$_2$CO— | oil | 568 (M + H$^+$) | D |
| 26 | d-γ-tocotrienyl N-t-Boc-sarcosinate | H | $CH_3$ | N-t-BOC-N(CH$_3$)CH$_2$CO— | oil | 582 (M + H$^+$) | D |
| 27 | d-α-tocotrienyl glycinate | $CH_3$ | $CH_3$ | NH$_2$CH$_2$CO— | oil | 482 (M + H$^+$) | D, E |
| 28 | d-α-tocotrienyl sarcosinate | $CH_3$ | $CH_3$ | CH$_3$NHCH$_2$CO— | oil | 496 (M + H$^+$) | D, E |
| 29 | d-γ-tocotrienyl glycinate | H | $CH_3$ | NH$_2$CH$_2$CO— | oil | 468 (M + H$^+$) | D, E |
| 30 | d-γ-tocotrienyl sarcosinate | H | $CH_3$ | CH$_3$NHCH$_2$CO— | oil | 482 (M + H$^+$) | D, E |
| 31 | d-α-tocotrienyl N,N-dimethylglycinate | $CH_3$ | $CH_3$ | (CH$_3$)$_2$NHCH$_2$CO— | oil | 510 (M + H$^+$) | F |
| 32 | d-γ-tocotrienyl N,N-dimethylglycinate | H | $CH_3$ | (CH$_3$)$_2$NHCH$_2$CO— | oil | 496 (M + H$^+$) | F |
| 33 | d-δ-tocotrienyl N,N-dimethylglycinate | H | H | (CH$_3$)$_2$NHCH$_2$CO— | oil | 482 (M + H$^+$) | F |

TABLE 7

| Compound No. | Compound Name | Salt | Apperance | Method |
|---|---|---|---|---|
| 34 | 2R-γ-tocopheryl phosphate disodium salt $R^3$ = H, $R^4$ = CH$_3$, $R^7$ = Na | Na | white crystalline | H |
| 35 | 2R-γ-tocopheryl methylphosphate $R^3$ = H, $R^4$ = CH$_3$, $R^7$ = CH$_3$ | — | oil | I |

| Compound No. | Mass spectrometry | $^1$H-NMR spectrum |
|---|---|---|
| 34 | 541 (M + 1) | (In CD$_3$OD) 7.13(1H, s), 2.71(2H, t), 2.19(3H, s), 2.05(3H, s), 1.77-1.05(26H, m, including 1.22(3H, s)), 0.89-0.85(12H, m) |
| 35 | 524 (M$^+$) | (In CDCl$_3$) 6.83(1H, s), 3.85(3H, s), 3.83(3H, s) 2.69(2H, m), 2.17(3H, s), 2.10(3H, s), 1.78-1.05(26H, m, including 1.24(3H, s)), 0.87-0.84(12H, m) |

Investigation of Inhibitory Effect for Ischemia-Reperfusion Brain Damage

Cerebral infarction is a progressive disease wherein various mechanisms of injuries take place in a domino fashion, because of a decrease in the cerebral blood flow, and the brain damage spreads from the ischemic core to the periphery. In particular, the oxidative stress and inflammatory response after the onset of the disease is strongly involved. Therefore, the treatment in the subacute and chronic stages after the onset of the disease is very important in view of the seriousness and QOL. Clinically speaking, a drug that is possible to inhibit ischemia-reperfusion damage, even if the start of administration is late after cerebral infarction, is awaited.

Thus, a model evaluated for therapeutic effect of ischemia-reperfusion brain damage was constructed by administering a drug after reperfusion in the MCA occlusion model, and the effect of the test compound as a therapeutic drug was investigated: the therapeutic effect evaluation model reflects the direct damage by reactive oxygen species (ROIs) and the process to the secondary oxidative stress and inflammatory response due to ROIs.

In addition, a drug was administered immediately before infarction and during infarction in the MCA occlusion model, and the effect as a preventive drug was also investigated.

(1) Evaluation Method for Preventive Effect of Ischemia-Reperfusion Brain Damage With the use of male ddY mice (25-30 g, 6-7 weeks old), middle cerebral artery (MCA) occlusion model mice were prepared according to the method of Koizumi et al. ("Strokes", Vol. 8, pp 1-8, 1986). The MCA occlusion was carried out for 4 hours, a test drug solution was intravenously administered twice, namely, immediately before infarction and 3 hours after infarction. Brain slice samples were prepared 24 hours after the start of infarction and stained with triphenyltetrazolium chloride (TTC staining), and then the cerebral infarct volume was measured from the brain slice samples by image processing.

(2) Evaluation Method for Therapeutic Effect of Ischemia-Reperfusion Brain Damage With the use of male ddY mice (25-30 g, 6-7 weeks old), middle cerebral artery (MCA) occlusion model mice were prepared according to the method of Koizumi et al. ("Strokes", Vol. 8, pp 1-8, 1986). The MCA occlusion was 4 hours, and a single dose of drug solution was intravenously administered 6 or 10 hours after the start of ischemia (i.e., 2 hours or 4 hours after reperfusion). Brain slice samples were prepared 24 hours after the start of infarction and stained with triphenyltetrazolium chloride (TTC staining), and then the cerebral infarct volume was measured from the brain slice samples by image processing.

Example 3

Preventive Effect of Farnesol (FO) and Farnesol N,N-Dimethylglycine Ester Hydrochloride (FODMG) on Ischemia-Reperfusion Brain Damage According to the above-described prevention evaluation method of ischemia-reperfusion brain damage, the effect of (2E,6E) farnesol (FO), (2E,6E) farnesol N,N-dimethylglycinate hydrochloride (FODMG), and the commercial drug edaravone on ischemia-reperfusion brain damage was evaluated.

The brain slice samples of MCA-occluded mice 24 hours after the occlusion are shown in FIG. 1. The infarct volume, 24 hours after the start of occlusion, determined by the image processing of the brain slice samples of MCA-occluded mice 24 hours after the occlusion is shown in FIG. 2. FO was dissolved in DMSO and intravenously administered, and FODMG was dissolved in water and intravenously administered.

A significant suppression of the infarct volume was not observed at 2 μmol/kg×2 doses of FO; however, the infarct volume was significantly suppressed at 20 μmol/kg×2 doses.

FODMG significantly suppressed the infarct volume at both doses of 2 μmol/kg×2 and 20 mmol/kg×2, and the effect was dependent on dosage. FODMG exhibited an excellent preventive effect on ischemia-reperfusion brain damage compared with FO.

On the other hand, edaravone significantly suppressed the infarct volume at 2 μmol/kg×2 doses; however, a significant effect was not observed at 20 μmol/kg×2 doses. Thus, it was shown that a beneficial effect was not observed at high dosage and that the range of effective dosage was narrow.

The effect of FODMG was dependent on the dosage, and the effective dosage range was wide; thus it is clear that FODMG is superior to edaravone.

Example 4

Therapeutic Effect of Farnesol N,N-Dimethylglycine Ester Hydrochloride (FODMG) on Ischemia-Reperfusion Brain Damage According to the above-described evaluation method of the therapeutic effect of ischemia-reperfusion brain damage, the therapeutic effect of FODMG on ischemia-reperfusion brain damage was evaluated by a single administration after 6 hours or 10 hours from the start of ischemia at a dosage (20 μmol/kg), wherein an effect was not observed with edaravone. FO was dissolved in DMSO and intravenously administered, and FODMG was dissolved in water and intravenously administered.

FODMG significantly suppressed the infarct volume by both single administrations after 6 hours and 10 hours from the start of ischemia (FIG. 3). FODMG can be intravenously administered, and it is clear that it can enormously extend the start of treatment from the onset of cerebral infarction.

Example 5

Preventive Effect of 2R-γ-Tocopherol N,N-Dimethylglycine Hydrochloride (γ-TDMG) on Ischemia-Reperfusion Brain Damage According to the above-described evaluation method of the preventive effect of ischemia-reperfusion damage, the preventive effect of γ-TDMG 2R-α-tocopherol (α-Toc), and γ-tocopherol (γ-Toc) on ischemia-reperfusion damage was evaluated. γ-TDMG was dissolved in an aqueous solution containing 15% propylene glycol and administered. α-Toc and γ-Toc were dissolved in DMSO and administered, respectively.

Figure 4:
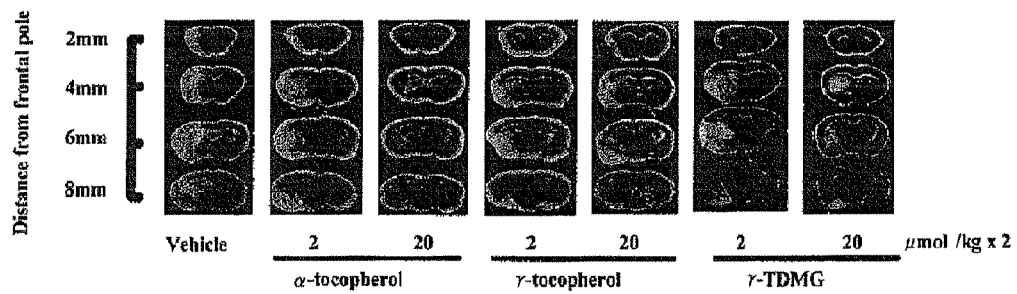
FIG. 4 illustrates the preventive effect of ischemic brain damage by the tocopherol derivative of the present invention.

The brain slice samples of MCA-occluded mice 24 hours after the start of occlusion are shown in FIG. 4. The infarct volume, 24 hours after the start of occlusion, determined by the image processing of the brain slice samples is shown in FIG. 5.

In the administration of α-Toc DMSO solution, the infarct volume was significantly suppressed at 20 μmol/kg×2 doses; however, a significant suppression of the infarct volume was not observed at 2 μmol/kg×2 doses.

In the administration of γ-Toc DMSO solution, the infarct volume was significantly suppressed at both doses of 2 μmol/kg×2 and 20 μmol/kg×2, and the significant suppression was achieved at 1/10 dosage of α-Toc.

In the intravenous administration of γ-TDMG aqueous solution, a significant suppression of the infarct volume was observed at both doses of 2 μmol/kg×2 and 20 mmol/kg×2, and the preventive effect of ischemia-reperfusion damage was displayed at a low dose, namely, 1/10 dosage of α-Toc. Thus, it was found that γ-TDMG had an excellent preventive effect on ischemia-reperfusion damage.

Example 6

Figure 6:
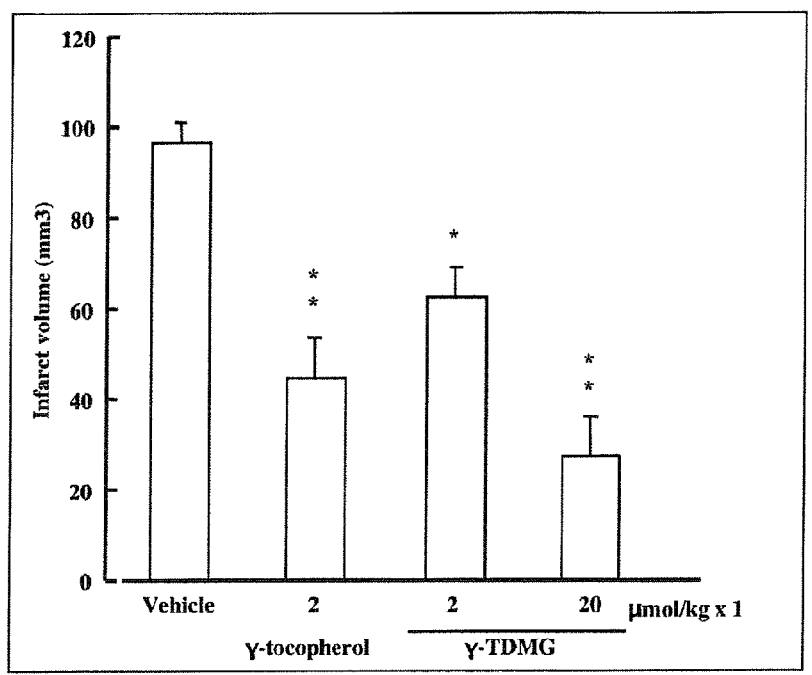
FIG. 6 illustrates the therapeutic effect of ischemic brain damage by the tocopherol derivative of the present invention.

Therapeutic Effect of 2R-γ-Tocopherol N,N-Dimethylglycine Hydrochloride (γ-TDMG) on Ischemia-Reperfusion Brain Damage The infarct volume, 24 hours after the occlusion, determined by the image processing of the brain slice samples of MCA-occluded mice 24 hours after the start of occlusion is shown in FIG. 6. γ-TDMG was dissolved in an aqueous solution containing 15% propylene glycol and administered. α-Toc and γ-Toc were dissolved in DMSO and administered, respectively.

Both the intravenous administration of γ-TDMG aqueous solution and the intravenous administration of γ-Toc DMSO solution significantly suppressed the infarct volume by a single dose of 2 μmol/kg or 20 μmol/kg after 6 hours from the start of ischemia.

In the cerebral infarction treatment, it is hoped that the time from infarction to the start of treatment is long. It is clear that the intravenous administration of γ-TDMG is possible and that γ-TDMG has a therapeutic effect by the administration after the onset of cerebral infarction.

Example 7

Preventive Effect of 2R-α-Tocotrienyl N,N-Dimethylglycine Hydrochloride α-T3DMG on Ischemia-Reperfusion Brain Damage According to the above-described evaluation method of the preventive effect of ischemia-reperfusion damage, the preventive effect of α-T3DMG on ischemia-reperfusion damage was evaluated. α-T3DMG was dissolved in an aqueous solution containing 15% propylene glycol and administered. α-Toc and 2R-α-tocotrienol (α-T3) were dissolved in DMSO and administered, respectively.

The infarct volume, 24 hours after the start of occlusion, determined by the image processing of brain slice samples is shown in FIG. 7.

In the intravenous administration of α-T3DMG aqueous solution, a significant suppression of the infarct volume was observed at both doses of 2 μmol/kg×2 and 20 μmol/kg×2, and it was clarified that α-T3DMG was effective at the same dosage as that of α-T3 DMSO solution, and that the inhibitory effect could be achieved at a low dose, namely, 1/10 dosage of α-Toc. Thus, α-T3DMG is useful as an excellent intravenously-administrable preventive agent for ischemia-reperfusion brain damage.

Example 8

Therapeutic Effect of 2R-α-Tocotrienyl N,N-Dimethylglycine Hydrochloride (α-T3DMG) on Ischemia-Reperfusion Brain Damage According to the above-described evaluation method of the therapeutic effect of ischemia-reperfusion brain damage, the effectiveness of α-T3DMG as a therapeutic drug was investigated. α-T3DMG was dissolved in an aqueous solution containing 15% propylene glycol and administered. α-Toc and 2R-α-tocotrienol (α-T3) were dissolved in DMSO and administered, respectively.

Figure 8:
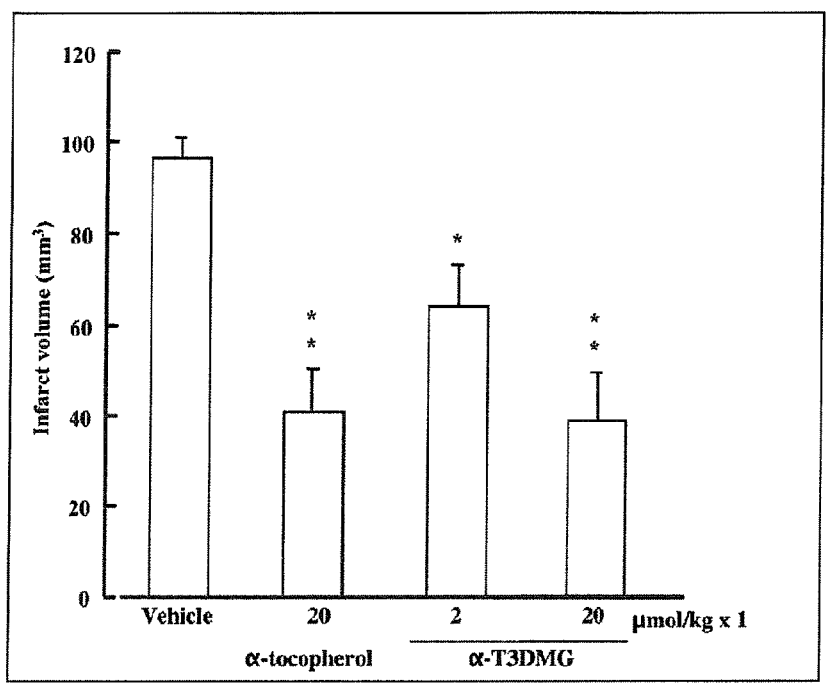
FIG. 8 illustrates the therapeutic effect of ischemia-reperfusion brain damage by the tocotrienol derivative of the present invention.

The infarct volume, 24 hours after the start of occlusion, determined by the image processing of brain slice samples of MCA-occluded mice 24 hours after the start of occlusion is shown in FIG. 8.

The intravenous administration of α-T3DMG aqueous solution significantly suppressed the infarct volume by a single dose of either 2 μmol/kg or 20 μmol/kg after 6 hours from the start of ischemia. It is clear that α-T3DMG, which can be intravenously administered, has a therapeutic effect by the administration after the onset of cerebral infarction.

Example 9

Figure 9:
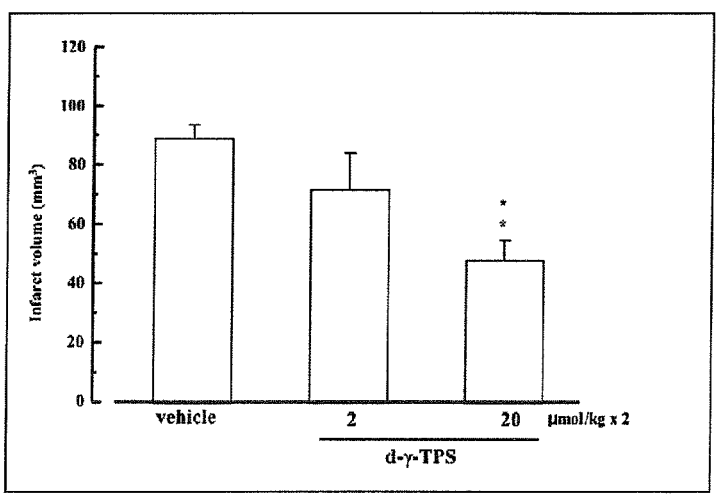
FIG. 9 illustrates the preventive effect of ischemia-reperfusion brain damage by the tocopherol derivative of the present invention.

Preventive Effect of 2R-γ-Tocopheryl Phosphate Disodium Salt (γ-TPS) on Ischemia-Reperfusion Brain Damage According to the above-described evaluation method of the preventive effect of ischemia-reperfusion damage, the preventive effect of γ-TPS on ischemia-reperfusion damage was evaluated. γ-TPS was dissolved in water and administered. The infarct volume, 24 hours after the start of occlusion, determined by the image processing of brain slice samples is shown in FIG. 9.

In the intravenous administration of γ-TPS aqueous solution, a significant effect was not observed at 2 μmol/kg×2 doses; however, a significant suppression of the infarct volume was observed at 20 μmol/kg×2 doses. Although the inhibitory effect was low compared with that of γ-Toc, the inhibitory effect comparable to that of α-Toc was observed. Thus, γ-TPS is effective as an intravenously-administrable preventive agent for ischemia-reperfusion brain damage.

Example 10

Figure 10:
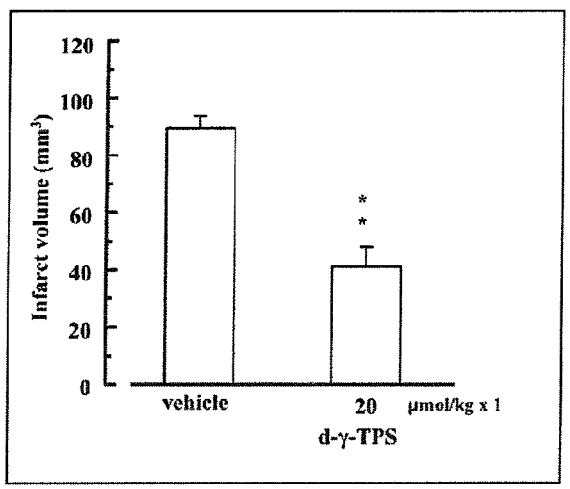
FIG. 10 illustrates the therapeutic effect of ischemia-reperfusion brain damage by the tocopherol derivative of the present invention.

Therapeutic Effect of 2R-γ-Tocopheryl Phosphate Disodium Salt (γ-TPS) on Ischemia-Reperfusion Brain Damage According to the above-described evaluation method of the therapeutic effect of ischemia-reperfusion brain damage, the effectiveness of γ-TPS as a therapeutic drug was investigated. γ-TPS was dissolved in water and administered. The infarct volume, 24 hours after the start of occlusion, determined by the image processing of brain slice samples of MCA-occluded mice 24 hours after the start of occlusion is shown in FIG. 10.

In the intravenous administration of γ-TPS aqueous solution, a significant suppression of the infarct volume was observed by a single dose of 20 μmol/kg after 6 hours from the start of ischemia. Thus, γ-TPS is effective as an intravenously-administrable therapeutic agent for ischemia-reperfusion brain damage.

The invention claimed is:

1. A farnesol carboxylic acid ester derivative represented by formula (1):

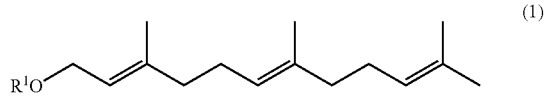

(1)

wherein $R^1$ represents a carboxylic acid residue having a nitrogen substituent selected from the group consisting of an N-acyl amino acid residue, an N-alkyl amino acid residue, an N,N-dialkyl amino acid residue, a pyridinecarboxylic acid residue, and a physiologically acceptable salt thereof, and the physiologically acceptable salt is selected from the group consisting of a hydrohalic acid salt, an alkylsulfonic acid salt, and an acidic sugar salt.

2. An inhibitor of ischemia-reperfusion disorder or a therapeutic agent of cerebral infarction, cerebral edema, or myocardial infarction, comprising, as an active ingredient, at least one substance selected from the group consisting of a farnesol carboxylic acid ester derivative, a pharmacologically acceptable salt thereof, a solvate thereof and a hydrate thereof, wherein said farnesol carboxylic acid ester derivative is represented by formula (2):

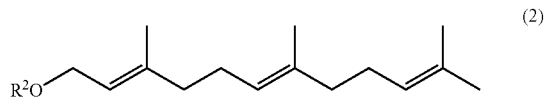

(2)

wherein $R^2$ represents a carboxylic acid residue having a nitrogen substituent selected from the group consisting of an amino acid residue, an N-acyl amino acid residue, an N-alkyl amino acid residue, an N,N-dialkyl amino acid residue, a pyridinecarboxylic acid residue, and a physiologically acceptable salt thereof, and the physiologically acceptable salt is selected from the group consisting of a hydrohalic acid salt, an alkylsulfonic acid salt, and an acidic sugar salt.

3. The farnesol carboxylic acid ester derivative according to claim 1, wherein $R^1$ is a residue selected from the group consisting of an N-alkyl amino acid residue, an N,N-dialkyl amino acid residue, and a physiologically acceptable salt thereof, and the physiologically acceptable salt is selected from the group consisting of a hydrohalic acid salt, an alkylsulfonic acid salt, and an acidic sugar salt, said alkyl being methyl.

4. The inhibitor of ischemia-reperfusion disorder or the therapeutic agent of cerebral infarction, cerebral edema, or myocardial infarction according to claim 2, wherein $R^2$ is a residue selected from the group consisting of an N-alkyl amino acid residue, an N,N-dialkyl amino acid residue, and a physiologically acceptable salt thereof, and the physiologically acceptable salt is selected from the group consisting of a hydrohalic acid salt, an alkylsulfonic acid salt, and an acidic sugar salt, said alkyl being methyl.

5. A farnesol carboxylic acid ester derivative selected from the group consisting of farnesol sarcosinate, farnesol N-tert-butoxycarbonylglycinate, farnesol N,N-dimethylglycinate, farnesol N,N-dimethyl-β-alaninate, farnesol N,N-diethyl-β-alaninate, farnesol N-tert-butoxycarbonylsarcosinate, and hydrochloric acid salts thereof.

6. The inhibitor of ischemia-reperfusion disorder or the therapeutic agent of cerebral infarction, cerebral edema, or myocardial infarction according to claim 2, wherein said farnesol carboxylic acid ester derivative is farnesol N,N-dimethylglycinate or its hydrochloric acid salt.

* * * * *